United States Patent [19]

Vargas, III

[11] Patent Number: 5,346,495
[45] Date of Patent: Sep. 13, 1994

[54] BIOMEDICAL CEMENT APPLICATOR

[76] Inventor: Joseph H. Vargas, III, Box 7118, RR #3, Woodstock Ave., Rutland, Vt. 05701

[21] Appl. No.: 202,731

[22] Filed: Feb. 28, 1994

[51] Int. Cl.$^5$ .............................................. A61F 5/04
[52] U.S. Cl. ...................................... 606/92; 606/93; 604/272
[58] Field of Search ................................... 606/92-95, 606/184, 185; 604/57, 264, 272

[56] References Cited

U.S. PATENT DOCUMENTS

| | | | |
|---|---|---|---|
| 3,112,743 | 12/1963 | Cochran et al. | 606/93 |
| 3,255,747 | 6/1966 | Cochran et al. | 606/93 |
| 4,627,434 | 12/1986 | Murray | 606/94 |
| 4,653,489 | 3/1987 | Tronzo | 606/93 |
| 4,815,454 | 3/1989 | Dozier, Jr. | 606/94 |
| 4,896,662 | 1/1990 | Noble | 606/92 |
| 4,935,008 | 6/1990 | Lewis, Jr. | 604/272 |
| 4,966,601 | 10/1990 | Draenert | 606/92 |

FOREIGN PATENT DOCUMENTS

3443167  6/1986  Fed. Rep. of Germany ........ 606/93

Primary Examiner—Ralph A. Lewis
Attorney, Agent, or Firm—John J. Welch

[57] ABSTRACT

A method and apparatus for applying methyl methacrylate under pressure into the top surface of a human tibial bone which apparatus is a solid molded one piece unit body with three rodlike extensions emanating from the body therefrom. A first rodlike extension has a solid cylindrically shaped head on its top side for receipt of a slaphammer and the long central axis of this extension is virtually co-axial with the long central axis of a second rodlike extension and sharp beveled end located at the base of the second rodlike extension just below a circular stop piece which beveled end for burrowing into bone is farther from the cylindrically shaped head than any other part of the one piece unit. The unit's third rodlike extension extends out and away from the first rodlike extension and has located atop it, a hollow head containing threading for receipt of the base of a cement carrying canister and with a hole in the center of the hollow head's bottom surface leading into a cement carrying canal running throughout this rodlike extension in a straight line and then in the same line through the body of the one piece unit to a point where an extension of the canal it courses downward leading to and through the beveled end.

6 Claims, 5 Drawing Sheets

BIOMEDICAL CEMENT APPLICATOR

I.

Your inventor, Joseph H. Vargas, III, M.D., respectfully submits this, his application for letters patent as respects his invention entitled, A Biomedical Cement Applicator.

II.

SPECIFICATIONS

A

Title of the Invention

The instant invention is entitled, A Biomedical Cement Applicator.

B

Cross References to Prior Applications

There are no prior or parent applications as respects the instant invention.

C

Federally Sponsored Research and Development

There is no federally sponsored research and development involvement as respects the instant invention.

D

Background of the Invention

1. Field of the Invention

The instant invention relates to those devices that serve to facilitate the introduction of cement-like bonding material into the human body in order to promote the stabilized positioning of prosthetic devices to be located within the human body.

2. Possible Prior Art

The following references constitute the arguably relevant art known to be somewhat within the realm of the field of the instant invention.

| Inventor | Invention | U.S. Pat. No. | Date |
| --- | --- | --- | --- |
| McKay et al | Bone Cement Applicator | 4,593,685 | 6/10/86 |
| Dozier, Jr. | Apparatus and Method for Injecting Bone Cement | 4,815,454 | 3/28/89 |
| Ziemann | Device for Ejecting or Taking in Liquid or Paste-Like Media | 4,973,334 | 11/27/90 |
| Chin | Method and Apparatus for Removing Pre-Placed Prosthetic Joints and Preparing for their Replacement | 5,156,606 | 10/20/92 |
| Maale | Intramedullary Rod Assembly for Cement Injection System | 4,653,487 | 3/31/87 |
| Park | Bone Cement Syringe | 4,751,921 | 6/21/88 |
| Brown | Method and Apparatus for Cementing an Acetabular Cup to an Acetabulum | 4,711,233 | 12/8/87 |

E

A Summary of the Invention

1. A Brief Description of the invention

The instant invention is a one piece moulded unit, the body of which has a top side. This top side is coextensive with the frontal portion of a first rodlike extension of the unit's body, the long central axis of which extension is perpendicular to the long axis of symmetry of the top side. The body of the unit also has two lateral sides both parallel to one another, the long axes of symmetry of each such side being perpendicular to the long axis of symmetry of the top side. Moulded atop the device's first rodlike extension is a solid cylindrically shaped disk, the diameter of which exceeds in length the diameter of the first rodlike extension. The posterior portion of the first rodlille extension is coextensive in a straight line with the rear side of the body of the unit. The rear side of the body of the unit terminates just below a stop piece moulded to and about the upper portion of the base of a second rodlike extension from the body of the unit, the long central axis of which is parallel to and nearly collinear with the extension of the long central axis of the first rodlike extension through the body of the unit. This circular stop piece is located in a plane perpendicular to the long central axis of this second rodlike extension. The body's top side is also coextensive with the rear portion of a third rodlike extension from the body of the unit. This third rodlike extension's long central axis juts out at an obtuse angle away from the lie of the long axis of symmetry of the top side. Atop this third rodlike extension is to be found moulded thereto a hollow cylindrical head containing inscribed about the whole of its interior, threading means for receipt of the threaded base of a methyl methacrylate containing canister equipped with a plunger. There is a hole in the center of the bottom side of the hollow cylindrical head that leads directly to a hollow canal, the diameter of which is the same as that of the hole. The hollow canal centered about the long central axis of the third rodlike extension and the extension of the axis through the body of the unit, courses in a straight line through the third rodlike extension and the body of the trait downward to the location at the base of the body of the trait where the second rodlike extension begins to form. The lateral portions of the third rodlike extension are respectively coextensive in straight lines with the lateral sides of the body of the unit. The frontal portion of the second rodlike extension in coextensive in a straight line with the frontal side of the body of the unit. The lateral portions respectively of the second rodlike extension are coextensive in a straight line with the lateral sides of the body of the unit. An extension of the hollow canal from the location at the base of the body of the unit where the form of the second rodlike extension begins runs through the whole of the center of the second rodlike extension centered on the long central axis of the second rodlike extension. The diameter of this extension of the canal is the same in length as that of the canal. Commencing at the bottom of the base of the second rodlike extension is a beveled end of the extension that is hollow throughout its interior broached by the termination of the extension of the hollow canal. The tip of the beveled end is typically sharp for facilitating a burrowing into the surface of bone, to wit, specifically the top surface of a human tibial bone.

The device is placed atop the top surface of a properly prepared tibial bone during knee replacement surgery in such a way that the device's beveled end is in direct contact with bone. Then a slaphammer in a surgeon's hand is made to strike the solid head of the first rodlike extension until the sharp beveled end is physically pounded into bone down to the level of the device's circular stop piece. This process of pounding and penetrating causes fluids and tissue found within the interstitial spaces of bone penetrated by the beveled end to be displaced under pressure. Methyl methacrylate bonding cement is then introduced under pressure from a cement holding plunger gun or canister; the threaded base of which is screwed into the threads inscribed in the hollow head atop the device's third rodlike extension and courses under such pressure through the hole in the bottom of the hollow head, down the hollow canal, and extension thereof and into the bony spaces circumscribed by said beveled end. Said cement is then found to be oozing and seeping from the top surface of said bone and, upon removal of the beveled end from the injection site, also from the sides of the bony mound now formed and surrounded by a ringed hollow space where the beveled end was formerly found.

For purposes of performing such a surgical procedure, the foregoing process is repeated a plurality of times atop the top surface of the properly prepared tibial bone. Then a layer of methyl methacrylate cement is applied over the whole top surface of the tibia which layer serves to hold fast a plate lain over the layer which plate functions as the permanent support base for an artificial knee. The cement layered atop of bone adheres to the bits of cement oozing and seeping from the top surfaces of the bone previously encased by the device's beveled end. Such layered cement also fills the hollow ringlike areas circumscribing such previously encased bone. Cement adheres to cement, to wit: layered cement atop the tibia adheres to cement oozing and seeping from top surfaces of previously encased bone, adheres to cement having led the hollow ring-like areas and this latter cement also adheres to cement oozing and seeping from the side of such pieces of previously encased bone. In this way, very strong cement to cement bonding enhances cement to bone bonding to ensure that the possibility of eventual positional loosening of the above-mentioned plate is greatly and indeed maximally minimized.

2. An Object of the Invention

The instant device is, respectfully submitted, truly new, useful and unique within the field of those devices utilized to impart bonding cement to bony surfaces during the performance of artificial knee replacement surgical procedures. The current art contemplates the use of such devices as serve to facilitate the bonding of cement to bone. Such bonding serves to ensure the positional integrity of support plates, etc., that are placed upon such cement, typically methyl methacrylate as is introduced to the surfaces of prepared bone, for example, the top surface of a surgically prepared human tibia. But, such bonding has limitations due to the fact that bone is dynamic, growing tissue and eventual degradation of bone to cement bonding is foreseeable. The instant device serves to overcome such limitations by facilitating the creation of cement to cement bonding in the form of cement footings of a sort that greatly enhance the effects of bone to cement bonding to thereby accomplish the primary objective, the instant device which is to minimize to the fullest possible extent any possibility of loose rang of a surgically cemented in support plate that could result in the need to undertake corrective surgical procedures much more often than would ever be desired. Loose support plates cause patients a goodly amount of pain and/or diminished mobility and expose them to the risks and costs associated with corrective surgery.

In view of the foregoing, the instant device which represents a radical departure from the prior art and is hence new and unique is likewise unquestionably useful in respect of accomplishing the objective of reducing remarkably post-op patient complications and the further objective namely of minimizing greatly the possibility that patient's will be exposed to the risks and costs of corrective surgery.

F

A Description of the Drawing

G

A Description of the Preferred Embodiment

Figures 1, 2, 3, 4, 5, 6, 7:
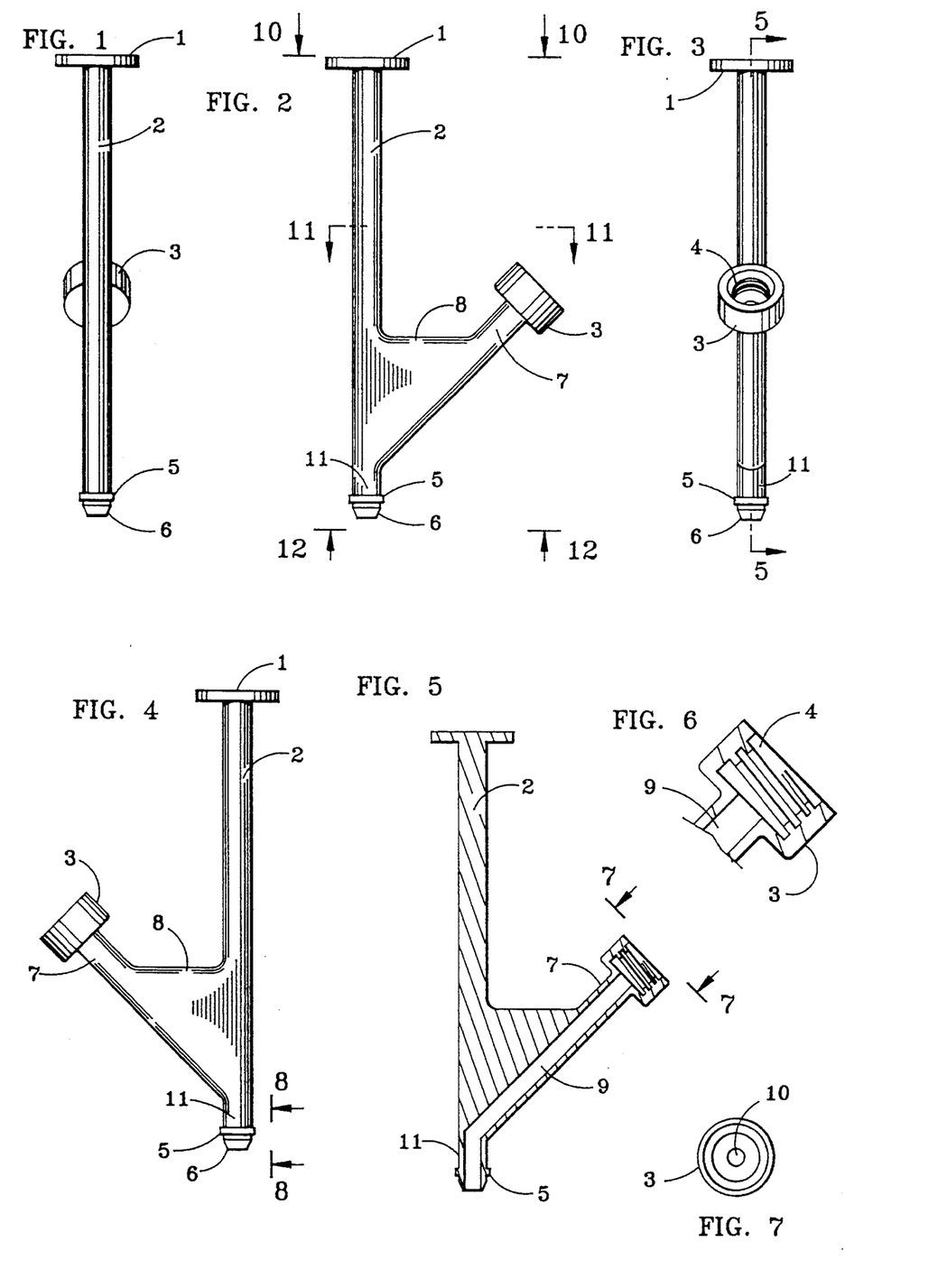
FIG. 1 is a plan view of the back portion of the instant device.
2.
FIG. 2 is a plan view of the first one of the two identical sides of the instant device.
3.
FIG. 3 is a plan view of the front portion of the instant device.
4.
FIG. 4 is a plan view of the second one of the two identical sides of the instant device.
5.
FIG. 5 is a longitudinal cross-sectional view of the instant device.
6.
FIG. 6 is an enlarged plan view of the hollow head of the third rod-like extension of the instant device.
7.
FIG. 7 is a cross-sectional view of the hole in the center of the bottom of the hollow head of the third rodlike extension of the instant device.
8.
Figure 8:
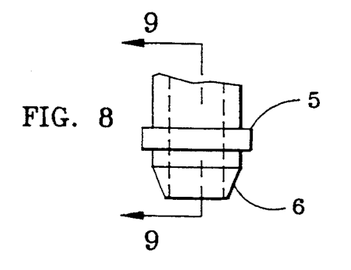
FIG. 8 is an enlarged plan view of the beveled end of the instant device.
9.
Figure 9:
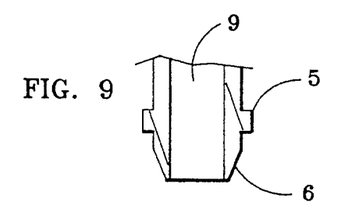
FIG. 9 is a cross-sectional view of the beveled end of the instant device.
10.
Figure 10:
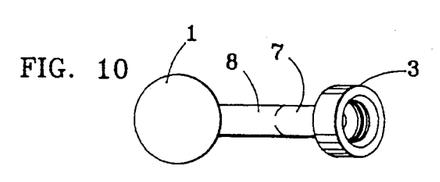
FIG. 10 is a top view of the instant device.
11.
Figure 11:
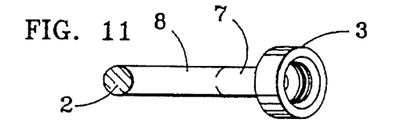
FIG. 11 is a view of the instant device after the device's first rod-like extension would have been cut away.
12.
Figures 12, 13, 14:
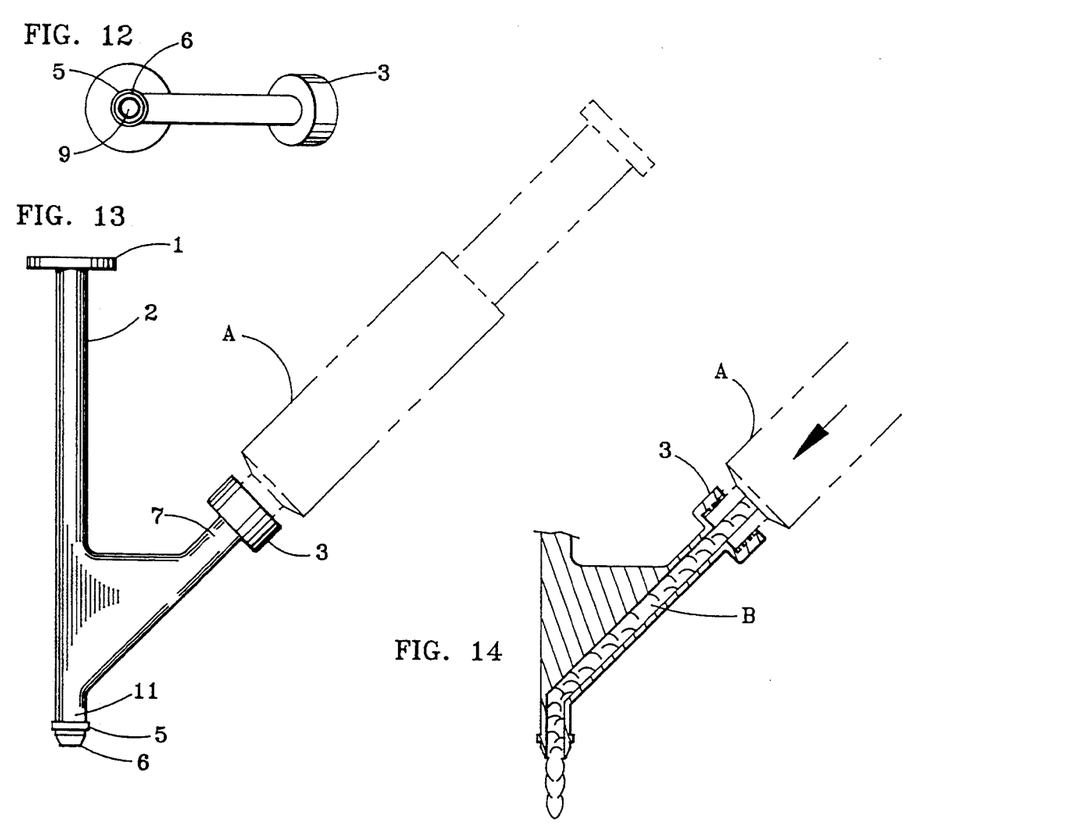
FIG. 12 is a bottom view of the instant device.
13.
FIG. 13 is a plan view of the instant device into the hollow head of which there has been threaded the threaded base of a cement injection canister.
14.
FIG. 14 is an isolated cross-sectional view of part of the instant device showing bonding cement injected under pressure from a cement injection canister through the device's hollow canal.
15.
Figure 15:
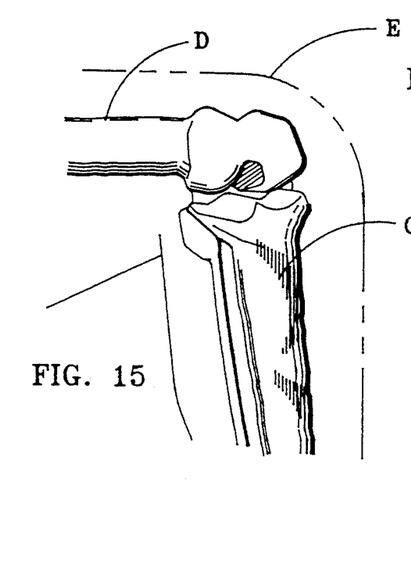
FIG. 15 shows the head of a human tibial bone and tibia in apposition to the base of a human femur in position to be operated on during knee replacement surgery.
16.
Figure 16:
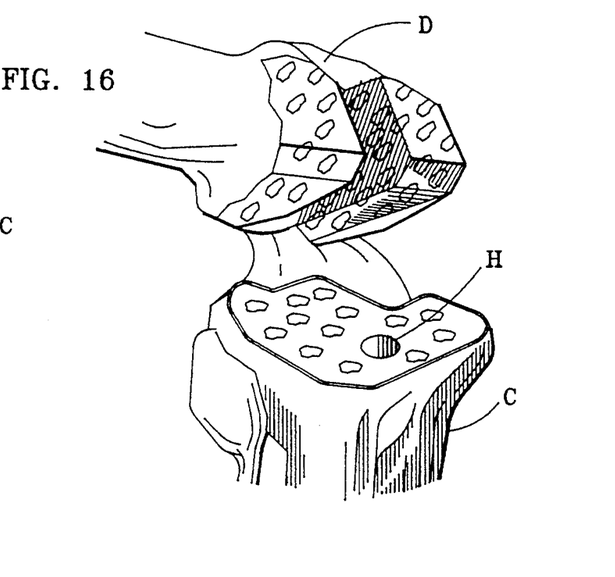
FIG. 16 shows surgically prepared femoral and tibial bone.
17.
Figure 17:
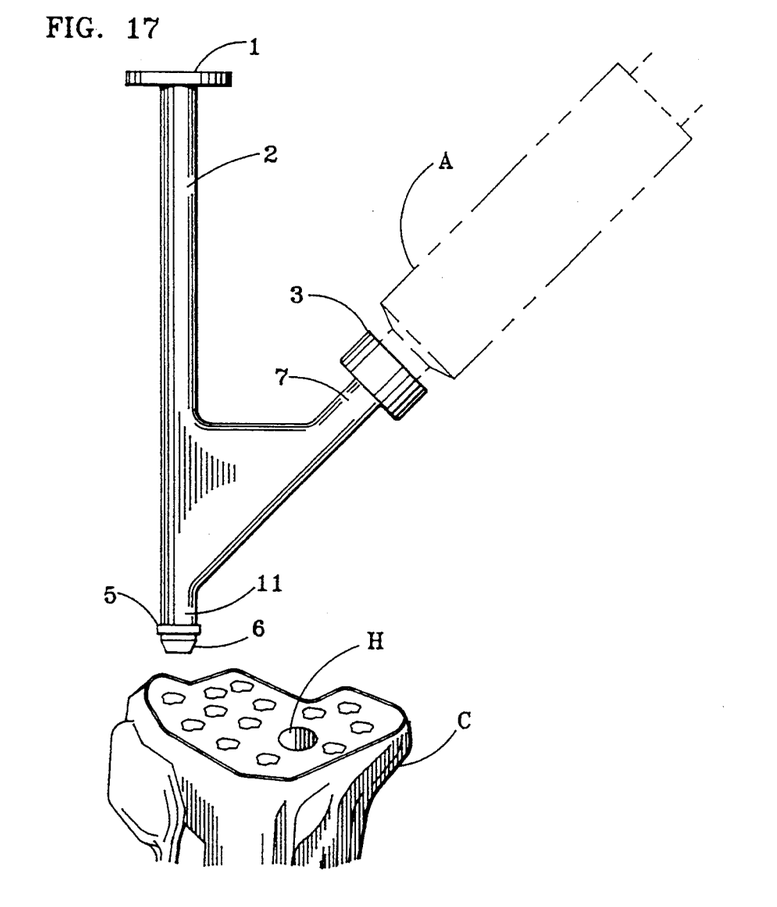
FIG. 17 shows the instant device connected to a cement injection canister in close apposition to a surgically prepared top surface of a human tibial bone.
18.
Figure 18:
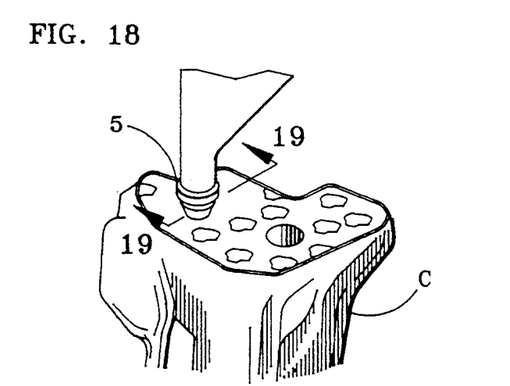
FIG. 18 shows in perspective view the instant device's beveled end in apposition to the top surface of a surgically prepared human tibial bone now with cement having been injected.
19.
Figure 19:
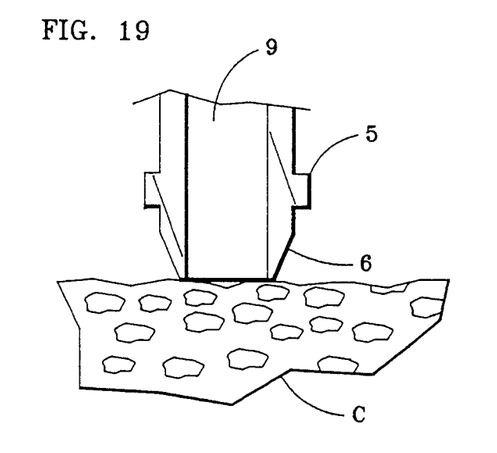
FIG. 19 shows in isolated cross-sectional view the instant device's beveled end in apposition to the top surface of a surgically prepared human tibial bone now with cement having been injected.
20.
Figure 20:
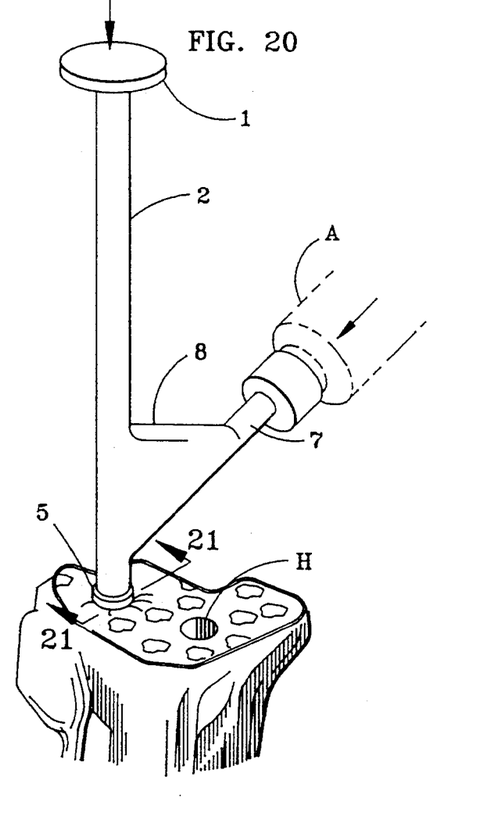
FIG. 20 shows in perspective view the instant device's beveled end hammered into a part of the top surface of a surgically prepared human tibial bone now with cement having been injected.
21.
Figure 21:
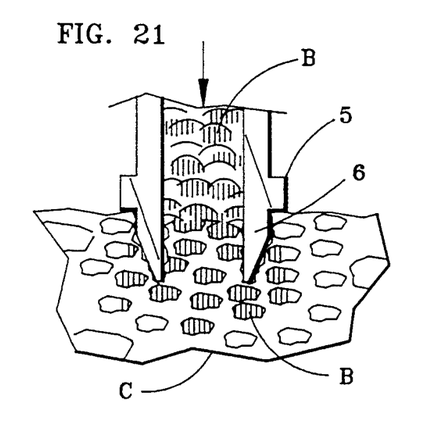
FIG. 21 shows in isolated cross-sectional view of the instant device's beveled end hammered into a part of the top surface of a surgically prepared human tibial bone now with cement having been injected.
Figure 22:
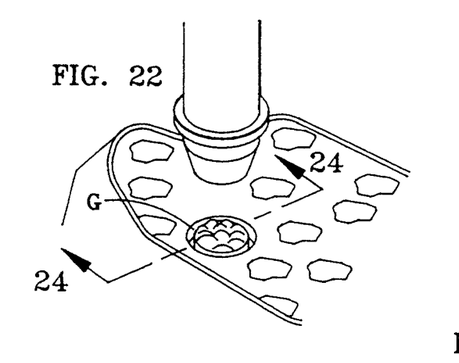
FIG. 22 shows in perspective view the portion of bone injected with cement and the ringlike space circumscribing such bone after removal of the instant device from the injection site.
Figure 23:
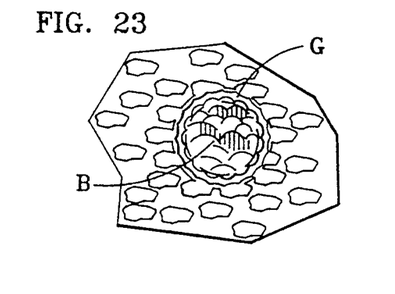
FIG. 23 shows in a top plan view the top surface of injected bone circumscribed by a ringlike space.
Figure 24:
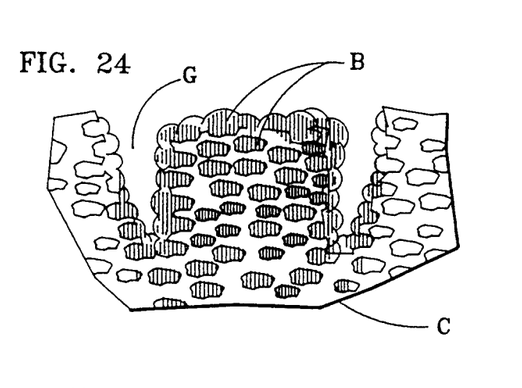
FIG. 24 shows in enlarged cross-sectional view the bone injected with cement circumscribed with a ringlike space.
Figure 25:
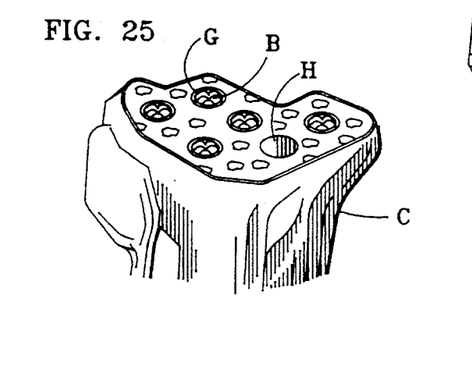
FIG. 25 shows in perspective view a plurality of injection sites on the top surface of a surgically prepared human tibial bone.
Figure 26:
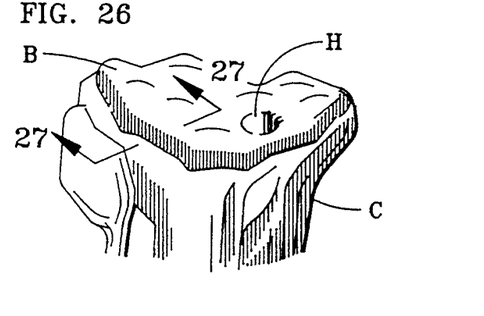
FIG. 26 shows a layer of bonding cement placed about the whole of the top surface of surgically prepared human tibial bone.
Figure 27:
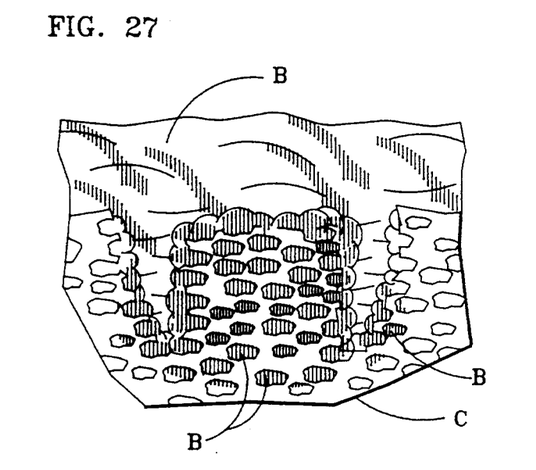
FIG. 27 shows in enlarged cross-sectional view, layered cement filling the ringlike space about previously injected bone as well as covering such bone.
Figure 28:
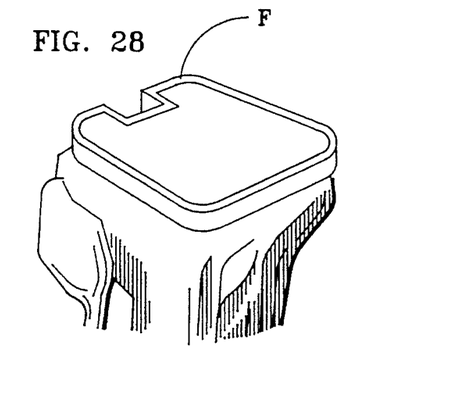
FIG. 28 shows in perspective view the plate placed upon cement to hold the plate in place on top of the top surface of surgically prepared human tibial bone.

The invention is a one piece unit moulded out of a hard material, typically a plastic type of material. FIG. 1, a rear view of the instant invention facilitates ready appreciation of the relationship between its solid head 1 atop its long first rodlike extension 2 and its circular stop 5 just above its beveled end 8 at the base of a short second rodlike extension 11. FIG. 2 shows the positional relationship of the rodlike extensions 2,11 and 7 to the body of the invention and likewise to one another. FIG. 3, a front view of the instant invention enables one to visualize the hollow head 3 with inscribed threading 4 that sits atop the invention's short third rodlike extension 7. FIG. 5 depicts the invention's hollow cement carrying canal 9. FIG. 7 shows hole 10 located in the center of the base of hollow head 3. FIG. 6 is an enlarged cross-sectional view of the head 3 with threading 4 showing the commencement therein of canal 9. FIG. 4 serves as a basis for illustrating via FIG. 8, the invention's circular stop 5 located just above its beveled end 6 within which is to be lotrod as per FIG. 9, the termination of the extension of canal 9. FIG. 10 shows in top view, the relationship between head 1, top surface 8, third rod 7 and hollow head 3. FIG. 11 shows a cross-sectional cut through rodlike extension 2 close to top surface 8. FIG. 12 is a view of the invention from the bottom looking up. FIG. 13 shows the threading of a cement carrying canister A into head 3 and FIG. 14, a cutaway view shows methyl methacrylate bonding cement B coursing down canal 9 under pressure through third rodlike extension 7 and the body of the unit and in a straight line down to a location in the body of the unit where canal 9 courses at an angle into an extension of canal 9 through second rodlike extension 11. FIG. 15 shows the base of a femoral bone D in a htnnan leg E in apposition to a tibial bone C in position for knee replacement surgery. FIG. 16 shows bone D and bone C appropriately cut and shaved in preparation for eventual placement upon the top surface of bone C, of a layer of methyl methacrylate B upon which there will ultimately be pressed for positional purposes a plate F as can be seen in FIG. 28. But, this protocol such as is essentially the one currently followed in respect of the performance of such knee replacement surgery promotes only bone to cement bonding. Notwithstanding the presence of an anchor hole H as seen in FIG. 16 for receipt on the top of the prepared tibial bone C of an extension foot at the base of a plate F lain atop a spread layer of cement B, there remains the ever present possibility to an accepted but nearly unacceptable degree of events loosening of the plate and the concomitant need for eventual corrective surgery in the face of patient pain and swelling at the operative site and likewise often sorely diminished patient weight bearing capability and range of motion. It is the matter of the potential for and indeed far too often the fact of such loosening that served to prompt the conceptualization and embodiment of the instant invention that operates to facilitate cement to cement bonding in addition to bone to cement bonding during the performance of such knee replacement surgery. Such enhanced bonding serves to markedly, indeed dramatically reduce any such prospective propensity for the eventual loosening of a plate F and the just noted problem that invariably emanate therefrom. FIG. 17 shows the instant device in apposition to tibial bone C after a cement injection canister A, serving to hold methyl methacrylate cement B, will have been threaded by way of threading at its base via threading 4 firmly into hollow head 3. The instant device is placed atop bone C as seen in FIG. 18 and FIG. 19. A slaphammer as per the arrow atop head 1 in FIG. 20 pounding on head 1 causes beveled end 6 of the device to burrow into bone C to the level of circular stop 5. Beveled end 6 is characteristically sharp at its tip so to enhance the process of such burrowing. Cement B under pressure from the plunger of canister A is forced down into a closed space within canal 9 as seen with reference once again to FIG. 14 and also as can be noted with reference to FIG. 21, an enlarged cutaway view of such a closed space. Cement B by virtue of such injection of the same under pressure into such closed space is forced down into the interstitial spaces within bone C and oozes and seeps through such spaces everywhere out the sides of and up through the top of bone C after removal of beveled end 6 from the application site as can be noted in FIG. 22, FIG. 23, a top view of an application site and FIG. 24 a cutaway view of an application site. Circumscribing bone C into which cement B has been injected is a ringlike space G formed by beveled end 6 burrowing into bone C to the level of circular stop 5. As per FIG. 25, the top of bone C is injected typically at five sites. Thereafter, as per FIG. 26, a layer of methyl methacrylate cement B is applied to the top of bone C after the top of bone C has been injected a plurality of times as noted above, with reference again to FIG. 25. FIG. 27 shows how ringlike space G is fried with cement B after such layering takes place. Cement B within space G bonds to cement B oozing and seeping out of the sides of bone C circumscribed by space G as seen, once again without cement in FIG. 24. Also, cement B layered as shown in FIG. 26 also bonds to cement B oozing and seeping out of the top of bone C as, once again, is shown in FIG. 23 prior to such layering taking place. Finally, a plate F as per FIG. 28 is placed on the layer of cement B that is now held in situ not only by bone to cement bonding but also by cement to cement bonding. It should be noted that in the cases of certain patients with hard or sclerotic tibia/bones, a cannulated drill bit with an external diameter the breadth of which equal the external diameter of the top of beveled end 6 just below circular stop 5 and an internal diameter, of the breadth of which equals the internal diameter of the top of beveled end 6 just below circular stop 5 could be fitted to a surgical drill and held in place by a chuck and could then serve to drill out ringlike space G after which drilling, beveled end 6 could then be inserted and cement B injected as noted above, and such a process could be performed a plurality of times.

Other embodiments contemplate rodlike extensions, one or more of which are uniformly triangular or rectangular in shape in combination with a triangularly, rectangularly or polygonally shaped solid head or stop piece.

In closing, the instant device is eminently reflective of a method for injecting methyl methacrylate into human bone under pressure by way of a canal within a solid body which canal terminates within the confines of a beveled end piece everywhere sharp-edged about its bottom and further which beveled endpiece, when driven into such bone to a depth determined by the position of a stop piece circumscribing a site at or above the top of the endpiece, serves to create the closed space essential to efficient permeation under pressure of such bone by such methyl methacrylate.

Also, the instant device could be utilized to inject methyl methacrylate into the head or base of a human femoral bone or humerus bone.

What is claimed is:

1. A one piece biomedical cement applicator, comprising.
   a. a body with a top side, a back side, the long axis symmetry of which is perpendicular to the long axis of symmetry of said top side, two parallel lateral sides, the respective long axis of symmetry of said two parallel lateral sides being perpendicular to said long axis of symmetry of said top side and a front side, the long axis of symmetry of which is inclined at an angle obtuse to the horizontal lie of said long axis of symmetry of said top side;
   b. a first rodlike extension of triform breadth throughout and extending from one end of said top side of said body, the long central axis of which said first rodlike extension is perpendicular to said long axis of symmetry of said top side, the posterior portion of which said first rodlike extension is coextensive in a straight line with said back side and the lateral portions of which are coextensive in straight lines respectively with said parallel lateral sides respectively;
   c. a solid cylindrically shaped disk covering the whole top or said first rodlike extension, the diameter of which said disk is greater in length than the said uniform breadth of said first rodlike extension, the perpendicular central axis of symmetry of which said disk is collinear with the long central axis of said first rodlike extension;
   d. a second cylindrically shaped rodlike extension of uniform diameter throughout and extending from the bottom of said body formed by the coalescence of said back side, said two parallel sides and said front side, the long central axis of which said second rodlike extension is perpendicular to said long axis of symmetry of said top side and nearly collinear with the long central axis of said first rodlike extension with the posterior portion of said second rodlike extension coextensive with said hack side, and the lateral portions of said second rodlike extension coextensive respectively with said parallel lateral sides respectively;
   e. a uniformly solid stop piece affixed to and circumscribing the whole of said second rodlike extension in proximity to the base of said second rodlike extension, the perpendicular axis of symmetry of which said stop piece is collinear with the long central axis of said second rodlike extension and the horizontal axis of symmetry of which said stop piece is greater in length than the length of the greatest breadth of said second rodlike extension;
   f. a hollowed out beveled end commencing at the base of said second rodlike extension, the bottom of which said beveled end is uniformly sharp edged;
   g. a third rodlike extension of uniform breadth throughout and extending from the other end of said top side of said body, the long central axis of which said third rodlike extension lies at an angle obtuse to the lie of said long axis of symmetry of said top side, and the inclination of the frontal portion of which said third rodlike extension is coextensive in a straight line with the inclination of said front side with the lateral portions of said third rodlike extension coextensive in straight lines respectively with said parallel later sides respectively;
   h. a hollow cylindrically shaped head atop said third rodlike extension, the central axis of symmetry of which said hollow cylindrically shaped head is collinear with the long central axis of said third rodlike extension;
   i. threading means inscribed about the whole of the inner walling of said hollow cylindrically shaped head;
   j. a first hole in the center of the bottom side of said hollow cylindrically shaped head;
   k. a hollow canal with uniform breadth throughout centered on the long central axis of said third rodlike extension which said canal commences at said first hole and courses on a straight line through the whole of said third rodlike extension and said body to a location within said body centered nearly on the long central axis of said rodlike extension;
   l. a cannular extension of said hollow canal with uniform breadth throughout and equal to the breadth of said hollow canal which said cannular extension commences at said location within said body and runs through the whole of said second rodlike extension centered on the long central axis of said second rodlike extension and terminating in a second hole in the bottom of said second rodlike extension which said second hole leads into said hollowed out beveled end.

2. The one piece biomedical cement applicator of claim 1 wherein said second rodlille extension is uniformly cylindrical in shape throughout with uniform diameter throughout.

3. The one piece biomedical cement applicator of claim 1 wherein said second rodlille extension is uniformly triangular in shape throughout with uniform altitude length and uniform base length throughout.

4. The one piece biomedical cement applicator of claim 1 wherein said second rodlille extension is triformly rectangular in shape throughout with uniform cross-sectional diagonal length throughout.

5. The one piece biomedical cement applicator of claim 1 wherein said second rodlille extension is uniformly polygonal in shape throughout with uniform cross-sectional diagonal length throughout.

6. A one piece biomedical cement applicator, comprising:
   a. a body with a top side, a back side, the long axis of symmetry of which is perpendicular to the long axis of symmetry of said top side, two parallel lateral sides, the respective long axes of symmetry of said two parallel lateral sides being perpendicular to said long axis of symmetry of said top side and a front side, the long axis of symmetry of which is inclined at an angle obtuse to the horizontal lie of said long axis of symmetry of said top side;
   b. a first cylindrically shaped rodlike extension of uniform diameter throughout and extending from one end of said top side of said body, the long central axis of which said first rodlike extension is perpendicular to said long axis of symmetry of said top side, the posterior portion of which said first rodlike extension is coextensive in a straight line with said back side and the lateral portions of which are coextensive in straight lines respectively with said parallel lateral sides respectively;
   c. a solid cylindrically shaped disk covering the whole top of said first rodlike extension, the diameter of which said disk is greater in length than the said uniform diameter of said first rodlike extension, the perpendicular central axis of symmetry of which said disk is collinear with the long central axis of said first rodlike extension;
   d. a second cylindrically shaped rodlike extension of uniform diameter throughout and extending from the bottom of said body formed by the coalescence of said back side, said two parallel sides and said front side, the long central axis of which said second rodlike extension is perpendicular to said long axis of symmetry of said top side and nearly collinear with the long central axis of said first rodlike extension and the posterior portion of which said second rodlike extension is coextensive in a straight line with said hack side, the lateral portions of which said second rodlike extension are coextensive in straight lines respectively with said parallel lateral sides respectively;
   e. a cylindrically shaped stop piece affixed to and circumscribing the whole of said second rodlike extension in proximity to the base of said second rodlike extension, the perpendicular axis of symmetry of which said stop piece is collinear with the long central axis of said second rodlike extension;
   f. a cylindrically shaped hollowed out beveled end commencing at the base of said second rodlike extension, the bottom of which said beveled end is uniformly sharp edged;
   g. a third cylindrically shaped rodlike extension of uniform diameter throughout and extending from the other end of said top side of said body, the long central axis of which said third rodlike extension lies at an angle obtuse to the lie of said long axis of symmetry of said top side, and the inclination of the frontal portion of which is coextensive in a straight line with the inclination of said front side with the lateral portions of said third rodlike extension coextensive in straight lines respectively with said parallel lateral sides respectively;
   h. a hollow cylindrically shaped head atop said third rodlike extension, the central axis of symmetry of which said hollow cylindrically shaped head is collinear with the long central axis of said third rodlike extension;
   i. threading means inscribed about the whole of the inner walling of said hollow cylindrically shaped head;
   j. a first hole in the center of the bottom side of said hollow cylindrically shaped head;
   k. a hollow canal with uniform breadth throughout centered on the long central axis of said third rodlike extension which said canal commences at said first hole and courses on a straight line through the whole of said third rodlike extension and said body to a location within said body centered nearly on the long central axis of said second rodlike extension;
   l. a cannular extension of said hollow canal with uniform breadth throughout and equal to the breadth of said hollow canal which said cannular extension commences at said location within said body and runs through the whole of said second rodlike extension centered on the long central axis of said second rodlike extension and terminating in a second hole in the bottom of said second rodlike extension which said second hole leads into said hollowed out beveled end.

* * * * *